US012491353B2

(12) United States Patent
Leibowitz

(10) Patent No.: US 12,491,353 B2
(45) Date of Patent: Dec. 9, 2025

(54) SYRINGE WITH DISINFECTING FEATURE

(71) Applicant: Becton, Dickinson and Company, Franklin Lakes, NJ (US)

(72) Inventor: Evan Leibowitz, Linden, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1144 days.

(21) Appl. No.: 17/619,095

(22) PCT Filed: Feb. 19, 2020

(86) PCT No.: PCT/US2020/018760
§ 371 (c)(1),
(2) Date: Dec. 14, 2021

(87) PCT Pub. No.: WO2020/172230
PCT Pub. Date: Aug. 27, 2020

(65) Prior Publication Data

US 2022/0233836 A1 Jul. 28, 2022

Related U.S. Application Data

(60) Provisional application No. 62/808,485, filed on Feb. 21, 2019.

(51) Int. Cl.
*A61M 39/02* (2006.01)
*A61M 3/02* (2006.01)
*A61M 39/00* (2006.01)

(52) U.S. Cl.
CPC ...... *A61M 39/0247* (2013.01); *A61M 3/0262* (2013.01); *A61M 2039/0018* (2013.01);
(Continued)

(58) Field of Classification Search
CPC ............ A61M 39/0247; A61M 3/0262; A61M 2039/0018; A61M 2039/0258; A61M 2039/0285; A61M 39/162; A61M 2005/3118; A61M 5/14; A61M 39/165; A61M 2005/1403; A61M 2210/12; A61M 2005/312; A61M 2005/3104; A61M 5/3414; A61M 35/003; A61M 2039/1033
See application file for complete search history.

(56) References Cited

U.S. PATENT DOCUMENTS 4,711,363 A 12/1987 Marino
4,738,376 A 4/1988 Markus
(Continued)

FOREIGN PATENT DOCUMENTS

CN 213852498 U 8/2021

OTHER PUBLICATIONS

PCT International Search Report and Written Opinion in PCT/US2020/018760 dated May 15, 2020, 13 pages.
(Continued)

*Primary Examiner* — Chelsea E Stinson
*Assistant Examiner* — Lei Gonzalez
(74) *Attorney, Agent, or Firm* — Servilla Whitney LLC

(57) ABSTRACT

Syringe assemblies comprising an absorbent pad containing disinfectant and a rotatable cap to ensure adherence to aseptic techniques for use in flush procedures for vascular access devices (VAD's) are described. Also described are methods of disinfecting vascular access devices.

19 Claims, 9 Drawing Sheets

(52) U.S. Cl.
CPC ............... *A61M 2039/0258* (2013.01); *A61M 2039/0285* (2013.01)

(56) References Cited

U.S. PATENT DOCUMENTS

| | | | | |
|---|---|---|---|---|
| 5,496,288 | A * | 3/1996 | Sweeney ............... | A61M 5/178<br>220/254.3 |
| 8,522,995 | B2 * | 9/2013 | Voss .................. | B65D 47/0885<br>215/250 |
| 8,784,388 | B2 | 7/2014 | Charles et al. | |
| 9,399,125 | B2 * | 7/2016 | Burkholz ............ | A61M 39/162 |
| 10,806,918 | B2 | 10/2020 | Charles et al. | |
| 10,953,218 | B2 | 3/2021 | Charles et al. | |
| 2008/0033371 | A1 | 2/2008 | Updegraff et al. | |
| 2011/0046603 | A1 | 2/2011 | Felsovalyi et al. | |
| 2012/0016318 | A1 | 1/2012 | Hoang et al. | |
| 2012/0123386 | A1 | 5/2012 | Tsals | |
| 2014/0148781 | A1 | 5/2014 | Tekeste | |
| 2015/0374968 | A1 | 12/2015 | Solomon et al. | |
| 2016/0101276 | A1 * | 4/2016 | Tekeste ................. | A61M 5/345<br>604/513 |
| 2018/0093082 | A1 * | 4/2018 | Adams ................ | A61M 35/003 |
| 2018/0237190 | A1 | 8/2018 | Iwasaki | |
| 2019/0099557 | A1 * | 4/2019 | Potdar ................. | A61M 5/3202 |
| 2019/0231984 | A1 * | 8/2019 | Mahmoodian ...... | A61M 5/3134 |
| 2019/0308006 | A1 | 10/2019 | Erekovcanski et al. | |
| 2021/0008283 | A1 | 1/2021 | Solo et al. | |
| 2021/0077805 | A1 | 3/2021 | Charles et al. | |

OTHER PUBLICATIONS

Final Office Action in U.S. Appl. No. 17/386,770 dated Jun. 16, 2023, 11 pages.

* cited by examiner

SYRINGE WITH DISINFECTING FEATURE

CROSS-REFERENCE TO RELATED APPLICATIONS

This application is the National Stage entry of PCT/US20/18760, filed on Feb. 19, 2020, which claims priority to U.S. Provisional Application. Ser. No. 62/808,485, filed Feb. 21, 2019, the entire disclosures of which are hereby incorporated by reference herein.

TECHNICAL FIELD

The present disclosure relates to syringe assemblies, and particularly to syringe assemblies comprising a disinfecting cap for use in flush procedures for vascular access devices (VAD's).

BACKGROUND

VAD's are commonly used therapeutic devices and include intravenous (IV) catheters. There are two general classifications of VAD's, peripheral catheters and central venous catheters. To ensure VAD's are used and maintained correctly, standards of practice have been developed, which include a cleaning procedure, commonly referred to as flushing a catheter.

VAD standards of practice usually recommend that flush procedures be performed after catheter placement, before fluid infusion, and before and after drug administration, blood sampling, transfusions and parenteral nutrition. The goal of these flush procedures is to confirm catheter patency, avoid drug incompatibilities, ensure complete drug dose administration, prevent thrombus formation and minimize the risk of blood stream infections. Flush procedures require different types and amounts of flush solutions. The most commonly used flush solutions are saline and/or heparin lock solution. The type of flush solution and amount vary depending on the specific type of catheter. Flush solution volumes between 5 and 10 ml are most common but can range from 1 ml to 20 ml.

For flush procedures, an IV line refers to a system that can include a VAD, a tubing set with clamp and a VAD connector as a termination. Common types of VAD connectors are covered by pierceable septums or pre-slit septums made of rubber or another elastomeric material, which permits insertion of a sharp needle cannula in order to infuse fluids into or to withdraw fluids from the catheter. Upon withdrawal of the needle cannula, the septum seals itself. Ports having pre-slit septums are used with blunt plastic cannula or the frusto-conically shaped tip of a syringe barrel. The syringe tip or the blunt plastic cannula (which is usually attached to a syringe) is gently pushed through the pre-slit septum to establish fluid communication.

IV valves, which are another type of VAD connector that do not require a needle having a sharp tip, are activated by the frusto-conically shaped tip of a syringe barrel to allow fluid communication between the interior of the syringe and the catheter. These valves may contain features for delivering fluid from a storage compartment in the valve to the catheter, and are referred to in the art as positive displacement valves. An example of such a valve is disclosed in U.S. Pat. No. 6,206,861.

Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal. Contamination can occur during drug mixing, attachment of a cannula, and insertion into the access hub. Presently, the risk to hospitals and patients is a substantial function of the diligence of the clinician performing the connection, and this diligence is largely uncontrollable.

A product currently available that aims to combat the problems associated with contaminated VAD connectors is the SwabCap®. This device disinfects a VAD connector by covering the connector and protecting it from touch and airborne contamination after the cap has been applied. As the SwabCap® is twisted onto a VAD connector, a foam pad inside the cap is compressed, releasing the isopropyl alcohol that passively disinfects the top and threads of the VAD connector while the cap is in place. Because the SwabCap® is a separate component, room for error exists so the cap may not be utilized after every step of the flush process. Thus, the cap does not ensure compliance with aseptic technique.

There is a need, therefore, for a flush syringe assembly that promotes compliance with aseptic technique by eliminating the additional swabbing and disinfecting steps.

SUMMARY

Aspects of the present disclosure are directed to a syringe assembly for use in flush applications and methods of disinfecting syringes. Syringe assemblies, for example, a flush syringe assembly according to a first aspect of the present disclosure comprise a barrel including a side wall having an outside surface, an inside surface defining a chamber for retaining fluid, an open proximal end, and a distal end including a distal wall with a distal tip extending distally therefrom having a first passageway therethrough in fluid communication with said chamber; a removable seal disposed on the peripheral distal surface; and a cap and an absorbent pad containing disinfectant disposed between the removable seal and the distal tip, the cap rotatable from a first position in which the distal tip is covered by the cap and a second position in which the distal tip of the barrel is exposed through the open distal end of the outer sleeve. In some embodiments, the assembly further comprises an outer sleeve slidably engaged with the outside surface of the barrel, the outer sleeve comprising an inner surface, an outer surface, and an open distal end comprising a peripheral distal surface, wherein relative sliding movement of the outer sleeve and the barrel to move distal tip of the barrel and the distal end of the outer sleeve closer together causes the distal tip to rotate the cap from the first position to the second position.

In as a second embodiment, a syringe assembly, for example, a flush syringe assembly comprises a barrel including a side wall having an outside surface, an inside surface defining a chamber for retaining fluid, an open proximal end, and a distal end including a distal wall with a distal tip extending distally therefrom having a first passageway therethrough in fluid communication with said chamber; and a cap covering the distal tip, the cap comprising a proximal side that covers the distal dip and a distal side including an absorbent pad mounted thereon, the cap pivotally movable from a first position in which the cap covers the distal tip to a second position in which the cap is moved away from the distal tip A second aspect of the present disclosure pertains to method of disinfecting a vascular access device. The method according to one embodiment comprises exposing an absorbent pad containing disinfectant at a distal end of a flush syringe assembly comprising a barrel having a distal tip covered by a cap, contacting the vascular access device with absorbent pad, and rotating the cap to expose the distal tip of the barrel.

DETAILED DESCRIPTION

Figure 1:
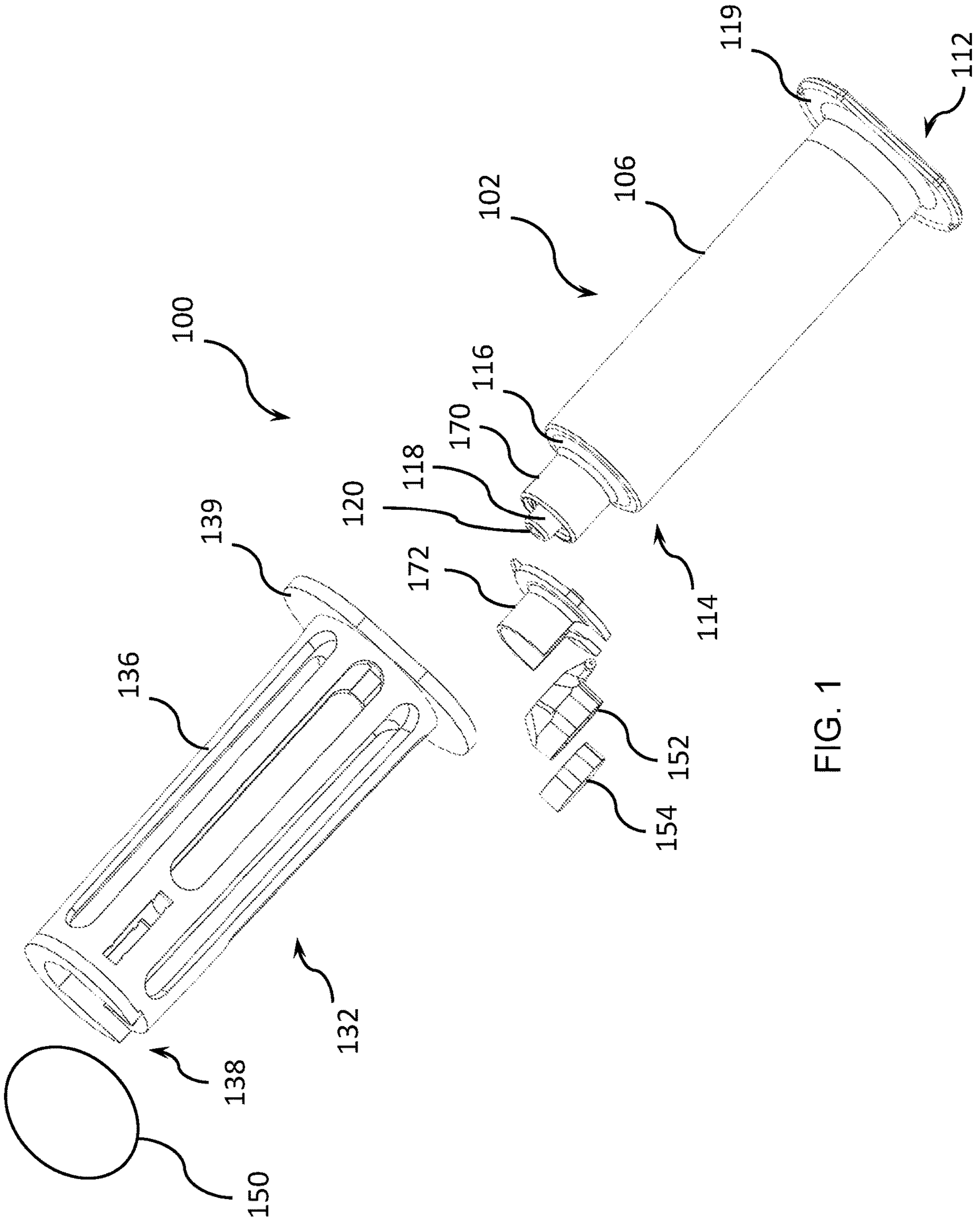
FIG. 1 is an exploded perspective view of a flush syringe assembly according to an embodiment of the present disclosure.

Before describing several exemplary embodiments of the disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

Reference to "flush syringe assembly" includes syringes that are indicated for use in the flushing of VADs. The practice of flushing ensures and maintains catheter patency and helps prevent the mixing of incompatible pharmaceuticals.

As used herein, the use of "a," "an," and "the" includes the singular and plural. As used herein, the term "catheter related bloodstream infection" or "CRBSI" refers to any infection which results from the presence of a catheter or IV line. As used herein, the term "microorganism" refers to a microbe or organism that is unicellular or lives in a colony of cellular organisms. Microorganisms are very diverse; they include, but are not limited to bacteria, fungi, archaea, and protozoans. Microorganisms are often the cause of CRBSIs. The most common microorganisms associated with CRBSIs include, but are not limited to, *Staphylococcus aureus* and *epidermis, Enterococcus faecalis, Escherichia coli, Pseudomonas aeruginosa*, and *Candida albicans.*

As used herein, the terms "antimicrobial agent" or "antimicrobial" refers to substances that kill or inhibit the growth of microorganisms such as bacteria, fungi, archaea, or protozoans. Antimicrobial agents either kill microbes, or prevent the growth of microbes. As used herein, the term "disinfectant" refers to antimicrobial substances that are used on non-living objects or outside the body, e.g., on the skin. In one or more embodiments, disinfectants or antimicrobial agent include, but are not limited to, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, dichlorobenzyl alcohol, dehydroacetic acid, hexetidine, triclosan, hydrogen peroxide, colloidal silver, and mixtures thereof.

As used herein, the terms "absorbent material" and "absorbent pad" refer to a material having capacity or tendency to absorb or soak up another substance. In one or more embodiments, the absorbent material or absorbent pad has a tendency to absorb a disinfectant or antimicrobial. Absorbent materials and absorbent pads may include sponges, absorbent cottons, foam, other absorbent fabrics, and synthetic polymer matrices.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the VAD. A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

According to one or more embodiments, a syringe assembly is provided that includes an absorbent material or an absorbent pad containing disinfectant or antimicrobial material that is moved away from the distal end of the syringe to expose the syringe distal tip. In one or more embodiments, the absorbent material is positioned such that there are minimal obstructions to the syringe distal tip, which allows the syringe distal tip to access ports that are typically difficult to access, such as Y-connectors. According to one or more embodiments, device activation so that the disinfectant is exposed is achieved by squeezing two parts of the syringe assembly together. This allows a user of the assembly to activate the device with one hand, which prevents interruption of workflow.

Referring now to FIGS. 1-9, a first embodiment of a flush syringe assembly 100 is shown. The flush syringe assembly 100 comprises a barrel 102 including a side wall 104 having an outside surface 106, an inside surface 108 defining a chamber 110 for retaining fluid. The barrel 102 further comprises an open proximal end 112, and a distal end 114 including a distal wall 116 with a distal tip 118 extending distally therefrom having a first passageway 120 therethrough in fluid communication with the chamber 110.

The embodiment shown in FIGS. 1-11 further comprises an outer sleeve 132 slidably engaged with the outside surface 106 of the barrel 102, the outer sleeve 132 comprising an inner surface 134, an outer surface 136, and an open distal end 138 comprising a peripheral distal surface 140. The syringe assembly 100 further comprises a removable seal 150 disposed on the peripheral distal surface 140. The apparatus further comprises a cap 152 and an absorbent pad 154 containing disinfectant disposed between the removable seal 150 and the distal tip, the cap 152 rotatable from a first position in which the distal tip 118 of the barrel 102 is covered by the cap 152 and a second position in which the distal tip 118 of the barrel 102 is exposed through the open distal end 138 of the outer sleeve 132.

Figure 2:
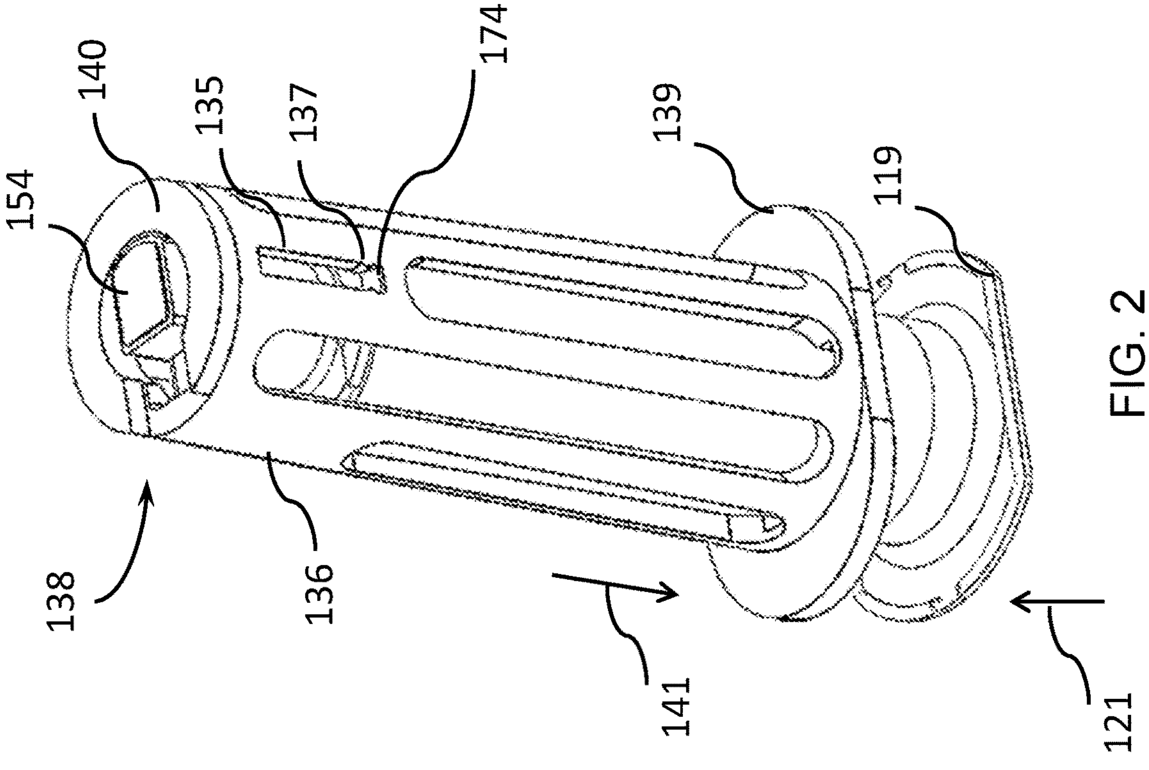
FIG. 2 is perspective view of a flush syringe assembly according to an embodiment of the present disclosure.
Figure 3:
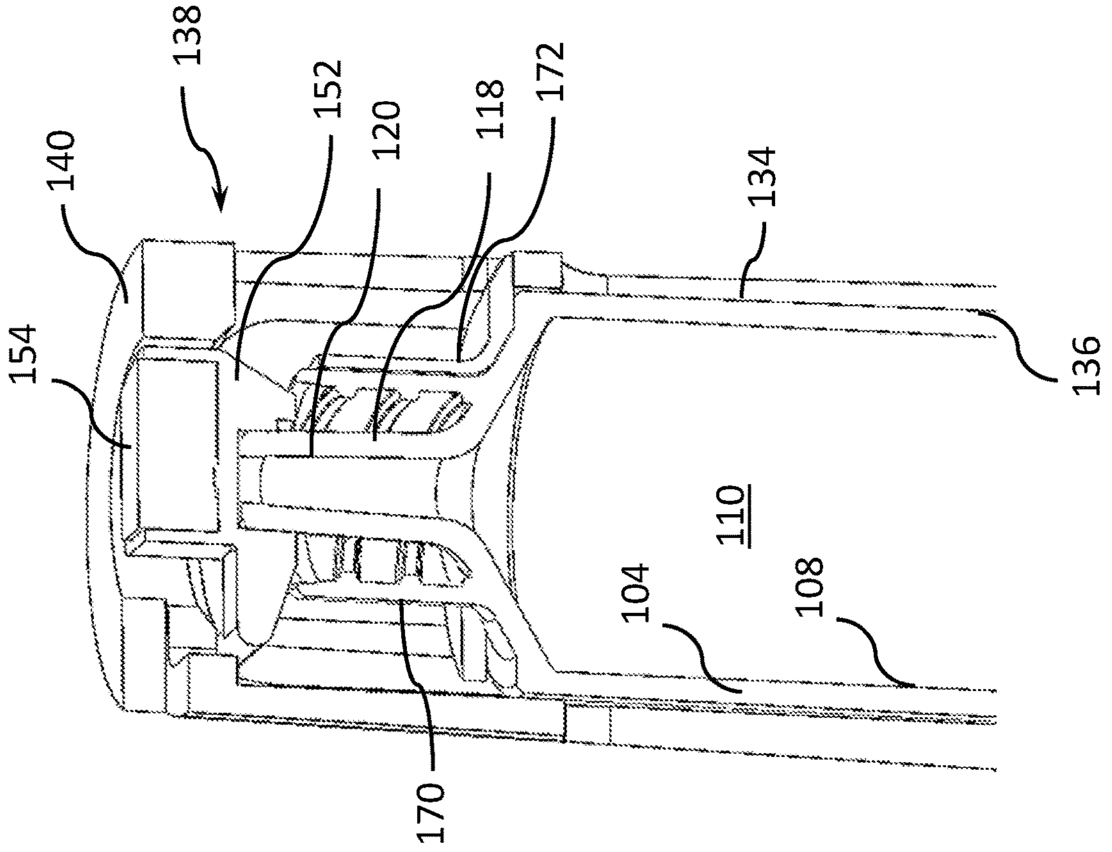
FIG. 3 is an enlarged partially cross-sectioned side elevation view of the flush syringe assembly of FIG. 2.
Figure 4:
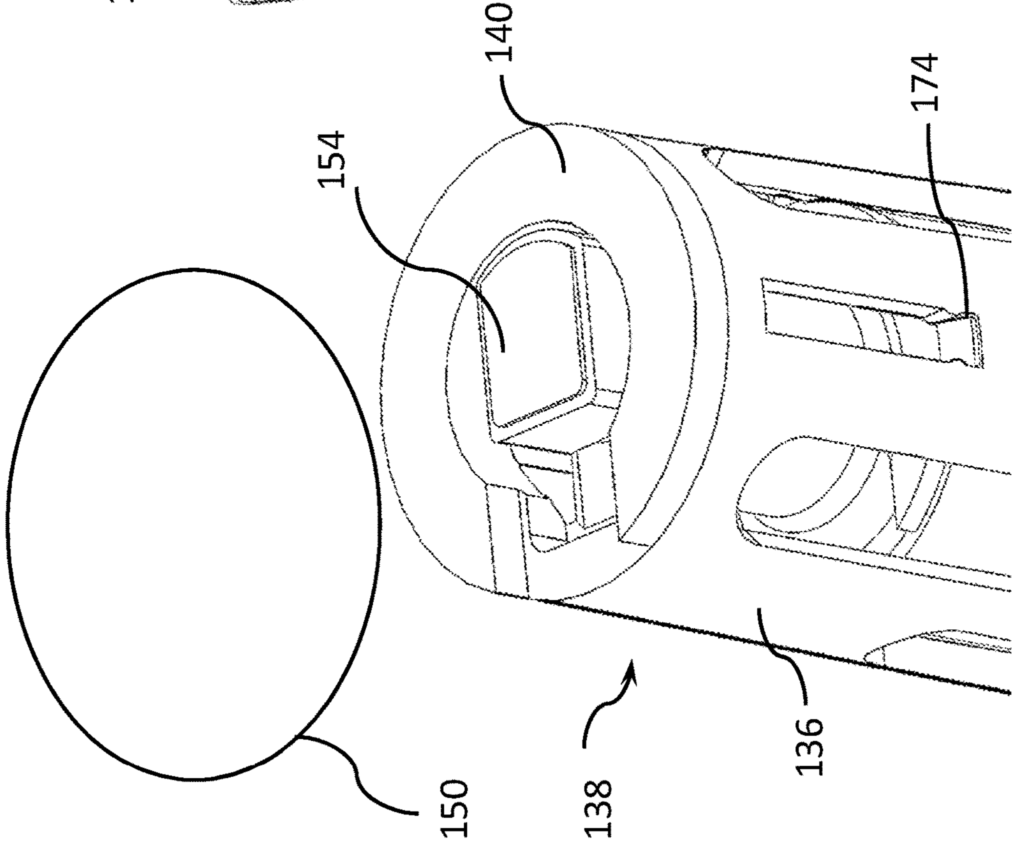
FIG. 4 if a partial perspective view showing the distal portion of the flush syringe assembly of FIG. 2.

FIGS. 2-4 show the flush syringe assembly 100 in the first position, with the distal tip 118 of the barrel 102 covered by the cap 152. In this embodiment, the cap 152 comprises a proximal side 151 and a distal side 153. In the first position, the proximal side 151 of the cap 152 covers the distal tip 118 of the barrel 102. In the embodiment shown in FIGS. 1-9, the cap 152 comprises a recess 156 on the proximal side 151 of the cap for receiving the distal tip 118 of the barrel when the cap 152 is in the first position, which is a folded down or covered position. Furthermore, in the embodiments shown in FIGS. 1-9, the absorbent pad 154 is located on the distal side 153 of the cap 152. In the embodiment shown, the distal side 153 of the cap 152 comprises a housing 158 which receives the absorbent pad 154.

Thus, in the embodiments shown in FIGS. 1-9, the syringe assembly comprising the barrel 102 includes the cap 152 covering the distal tip 118 of the barrel 102, with the cap 152 including a proximal side 151 that covers the distal tip 118 and a distal side 153 including the absorbent pad 154 mounted thereon. The cap 152 is pivotally movable from a first position in which the cap 152 covers the distal tip 118 to a second position in which the cap 152 is moved away from the distal tip 118. In some embodiments, the cap 152 is rotatably disposed between the distal tip 118 and the open distal end 138 of the outer sleeve.

Figure 5:
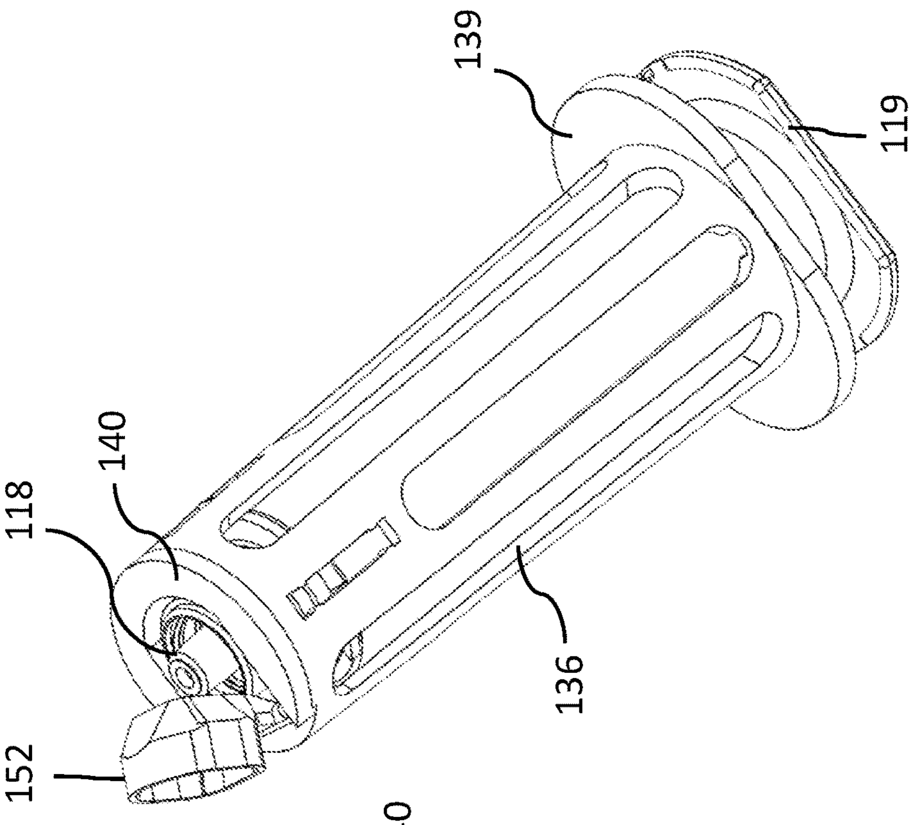
FIG. 5 is a perspective view of the flush syringe of FIG. 2 with the cap extended from the distal end of the flush syringe.
Figure 7:
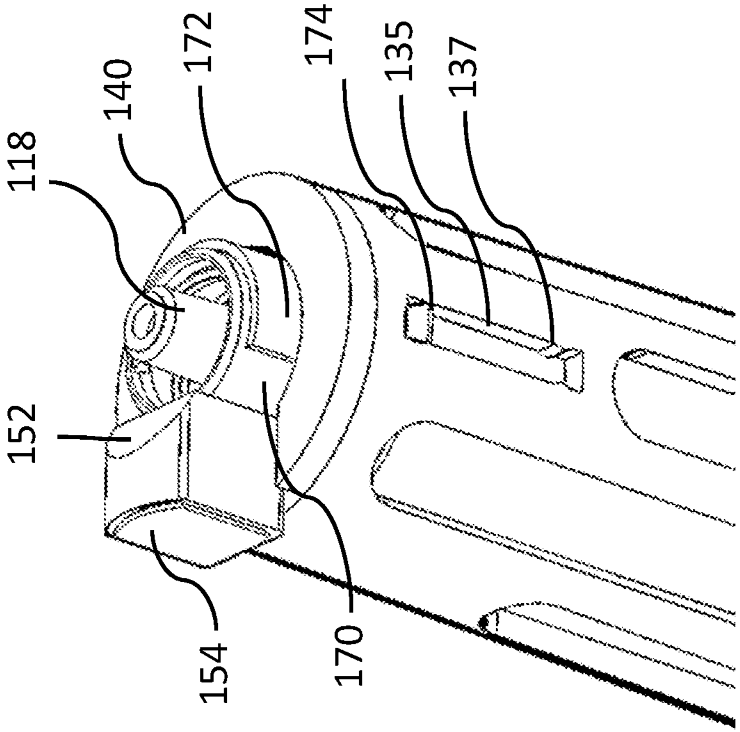
FIG. 7 is a partial perspective view of the flush syringe of FIG. 2 with the cap extended from the distal end of the flush syringe.
Figure 6:
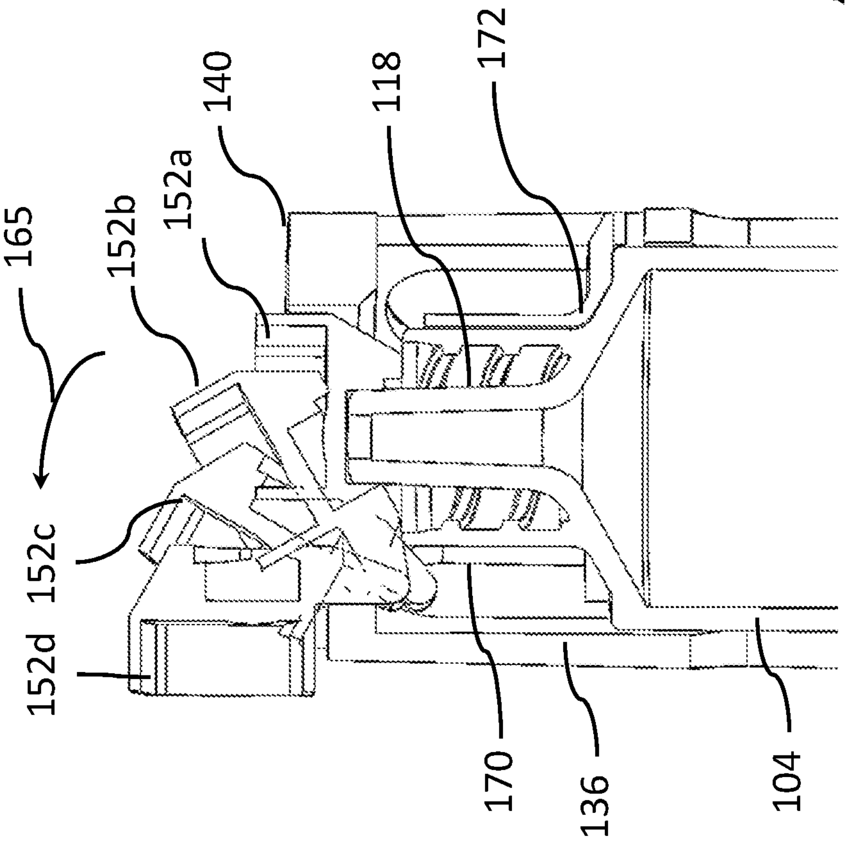
FIG. 6 is an enlarged partially cross-sectioned side elevation of the flush syringe of FIG. 2 with the cap extended from the distal end of the flush syringe.
Figure 8A:
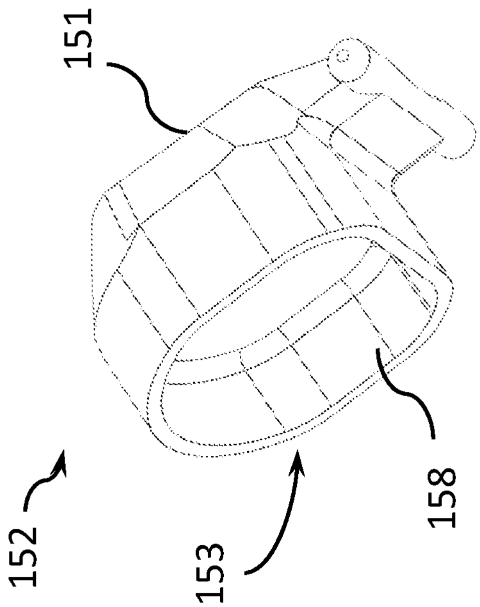
FIG. 8A is a perspective view of the distal side the cap of the flush syringe of FIG. 2.
Figure 8B:
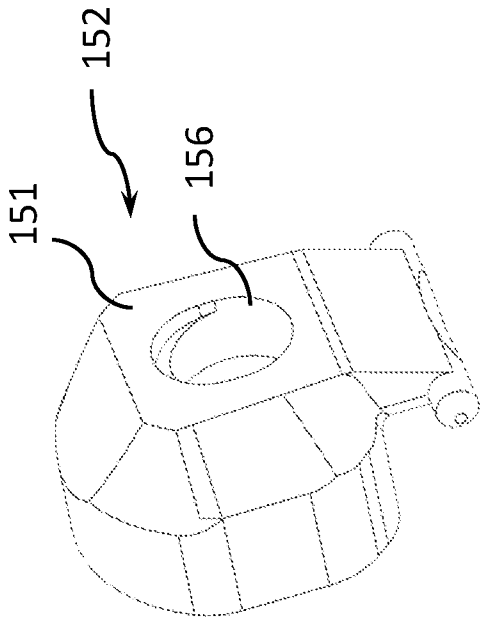
FIG. 8B perspective view the proximal side the cap of the flush syringe of FIG. 2.
Figure 9:
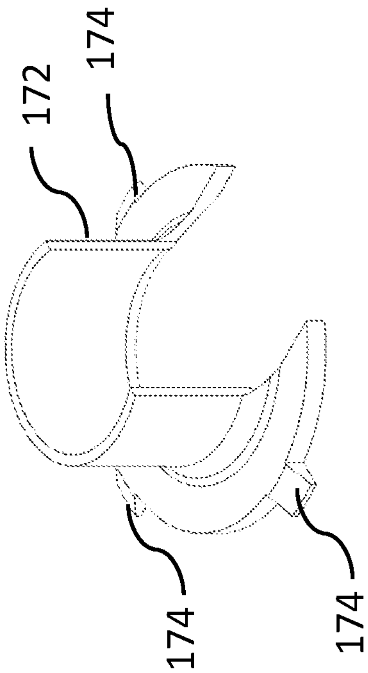
FIG. 9 is a perspective view of the alignment collar of the flush syringe of FIG. 2.

Referring now to FIGS. 5-7, relative sliding movement of the outer sleeve 132 and the barrel 102 moves the distal tip 118 of the barrel 102 and the open distal end 138 of the outer sleeve 132 closer together, which pushes the distal tip 118, causing the distal tip to rotate the cap 152 from the first position to the second position. FIG. 5 shows the cap 152 rotated in the direction of arrow 165 from the first position 152*a* in which the cap 152 covers the distal tip 118, to position 152*b* as the cap 152 is rotated off of the distal tip to position 152*c* and then position 152*d* where the cap 152 is in the uncovered position and the distal tip 118 is exposed as shown in FIG. 7. The relative sliding movement of the outer sleeve 132 and the barrel occurs when a user of the syringe assembly applies proximally directed force (in the direction of arrow 141 in FIG. 2) to the outer sleeve flange 139 while applying distally directed force (in the direction of arrow 121 in FIG. 2) to the barrel flange 119. According to one or more embodiments, a user can clean a VAD with the syringe assembly 100 and then connect the syringe assembly to the VAD using one hand. For example, a user can hold the syringe assembly with cap in the first position as shown in FIGS. 2-4 by gripping the outer sleeve between the index finger and middle finger of their hand. The user can then move the cap 152 and absorbent pad 154 out of the way by gripping the outer sleeve 132, applying the proximally directed force to the outer sleeve flange 139 by placing the outer sleeve between the user's fingers and pressing the barrel flange 119 into the palm of the user's hand or thumb as desired, which applies the distally directed force to the barrel flange 119. The user of the syringe assembly 100 applying the forces in this manner squeezes the outer sleeve flange 139 and barrel flange 119 towards each other, moving the cap 152 off of the distal tip 118 and exposing the distal tip 118, which can then be connected to a VAD.

The syringe assembly 100 is further shown as comprising a connection collar 170 surrounding the distal tip 118 and an alignment collar 172 coaxial with the connection collar 170, the alignment collar 172 comprising a peripheral tab 174 that engages the outer sleeve 132. The outer sleeve 132 comprises a slot 135 that cooperates with the peripheral tab 174 to align the cap 152 with the open distal end 138 of the outer sleeve 132 and to guide relative sliding movement between the barrel 102 and the outer sleeve 132. In the embodiment shown and as best seen in FIG. 7, the slot 135 in the outer sleeve comprises a detent 137 to prevent unintended relative movement of the syringe barrel 102 and the outer sleeve 132. FIGS. 2 and 4 show the peripheral tab 174 below the detent 137 in the slot 135, which holds the assembly in the ready to use position. The peripheral tab 174 and the detent 137 in the slot 135 are configured so that the user must exert a sufficient amount of force to advance the peripheral tab 174 past the detent 137, causing the cap to move from the first position to the second position. FIG. 7 shows the peripheral tab 174 after the peripheral tab 174 has been advanced past the detent 137, having moved in a distal direction (indicated by arrow 121 in FIG. 2), advancing the distal tip 118 past the open distal end 138 of the outer sleeve so that the distal tip can be connected to a VAD. In one or more embodiments, the alignment collar 172 can comprise a plurality of peripheral tabs 174, for example, two, three, or more. The outer sleeve 132 can similarly comprise a plurality of slots 135 which cooperate with the peripheral tabs 174 to guide the outer sleeve 132 and the barrel 102 during relative sliding motion.

Referring now to FIGS. 10-17, a second embodiment of a flush syringe assembly 200 is shown. The flush syringe assembly 200 comprises a barrel 202 including a side wall 204 having an outside surface 206, an inside surface 208 defining a chamber 210 for retaining fluid. The barrel 102 further comprises an open proximal end 112, and a distal end 114 including a distal wall 216 with a distal tip 218 extending distally therefrom having a first passageway 220 therethrough in fluid communication with the chamber 210.

The embodiment shown in FIGS. 10-17 further comprises an outer sleeve 232 slidably engaged with the outside surface 206 of the barrel 202, the outer sleeve 232 comprising an inner surface 234, an outer surface 236, and an open distal end 238 comprising a peripheral distal surface 240.

The syringe assembly 200 further comprises a removable seal 250*a* disposed on the peripheral distal surface 240. The apparatus further comprises a cap 252 and an absorbent pad 254 containing disinfectant disposed between the removable seal 250 and the distal tip. The embodiment of FIGS. 10-17 further comprises a fixed seal 250*b* disposed between the cap 252 and the absorbent pad 254. The cap 252 is rotatable from a first position in which the distal tip 218 of the barrel 202 is covered by the cap 252 and a second position in which the distal tip 218 of the barrel 202 is exposed through the open distal end 238 of the outer sleeve 232.

Figure 11:
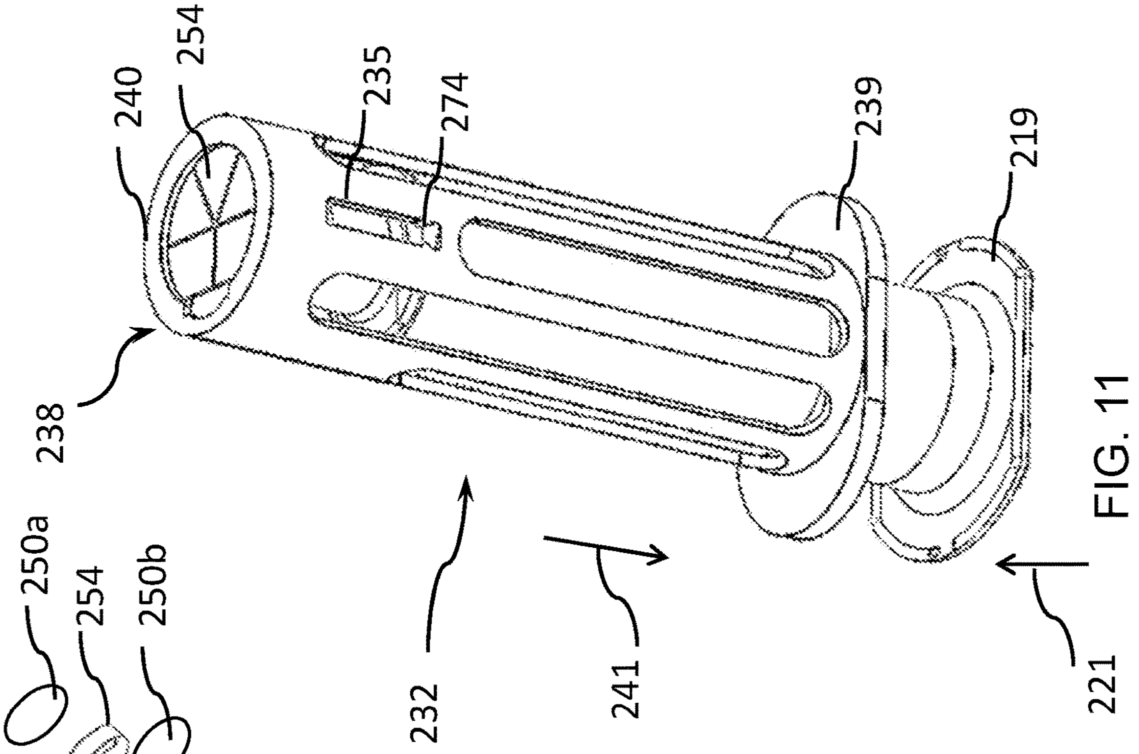
FIG. 11 is perspective view of a flush syringe assembly according to the second embodiment of the present disclosure.
Figure 10:
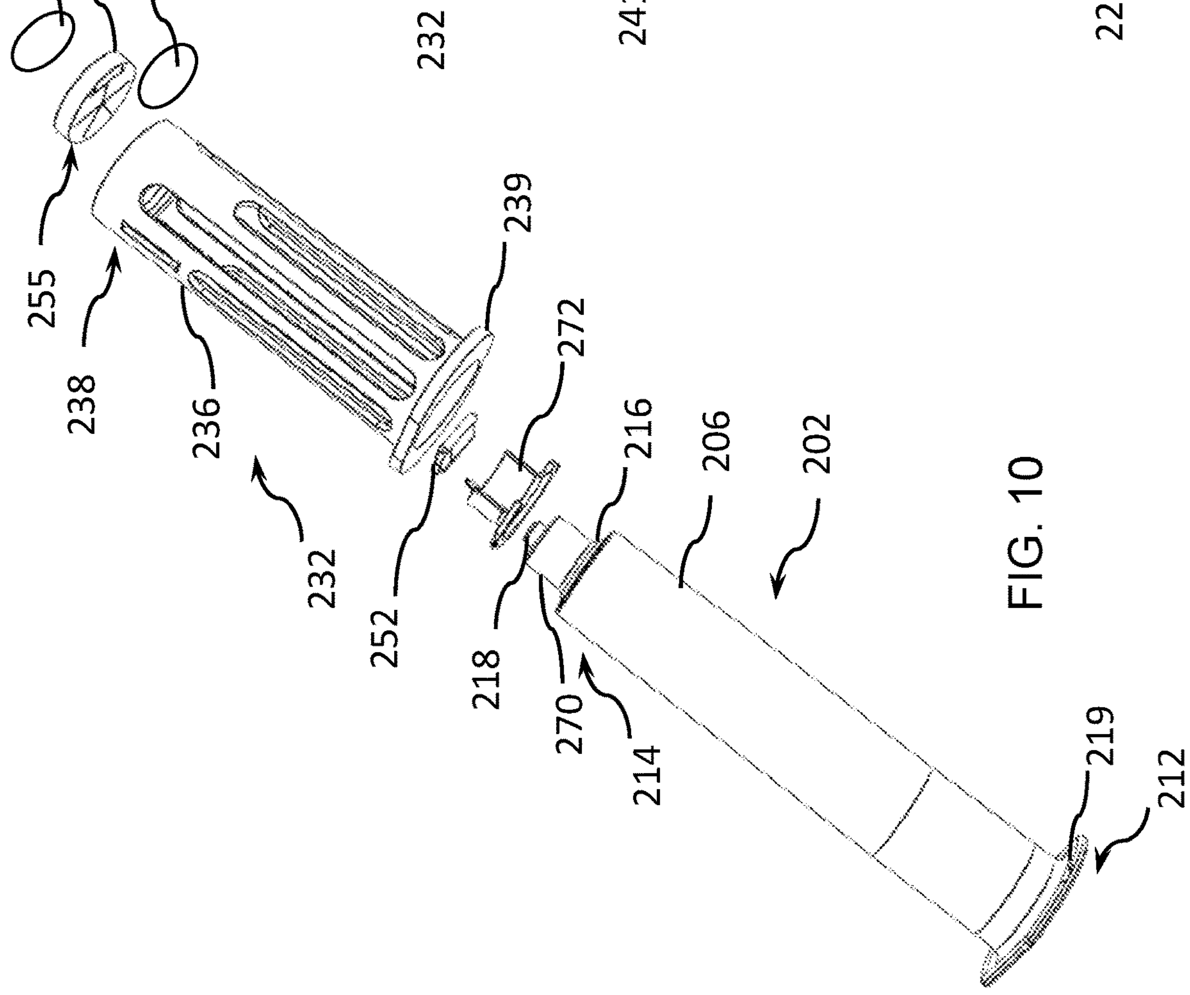
FIG. 10 is an exploded perspective view of a flush syringe assembly according to a second embodiment of the present disclosure.
Figure 13:
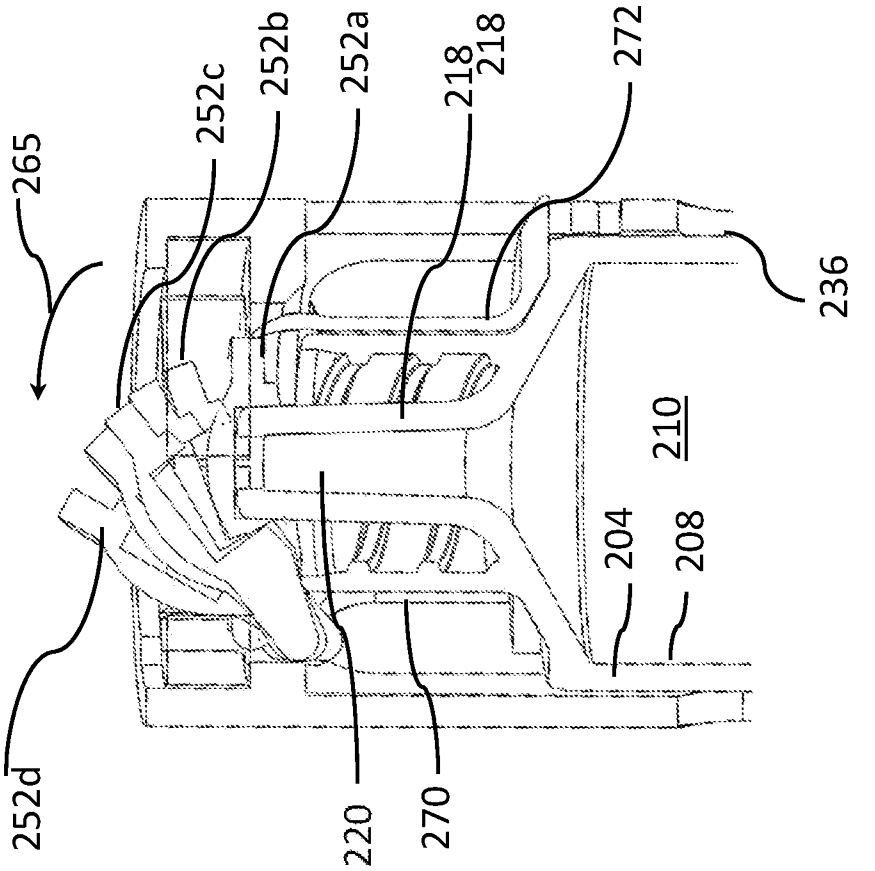
FIG. 13 is an enlarged partially cross-sectioned side elevation of the flush syringe assembly of FIG. 11 with the cap shown moving from a retracted to an extended position.
Figure 12:
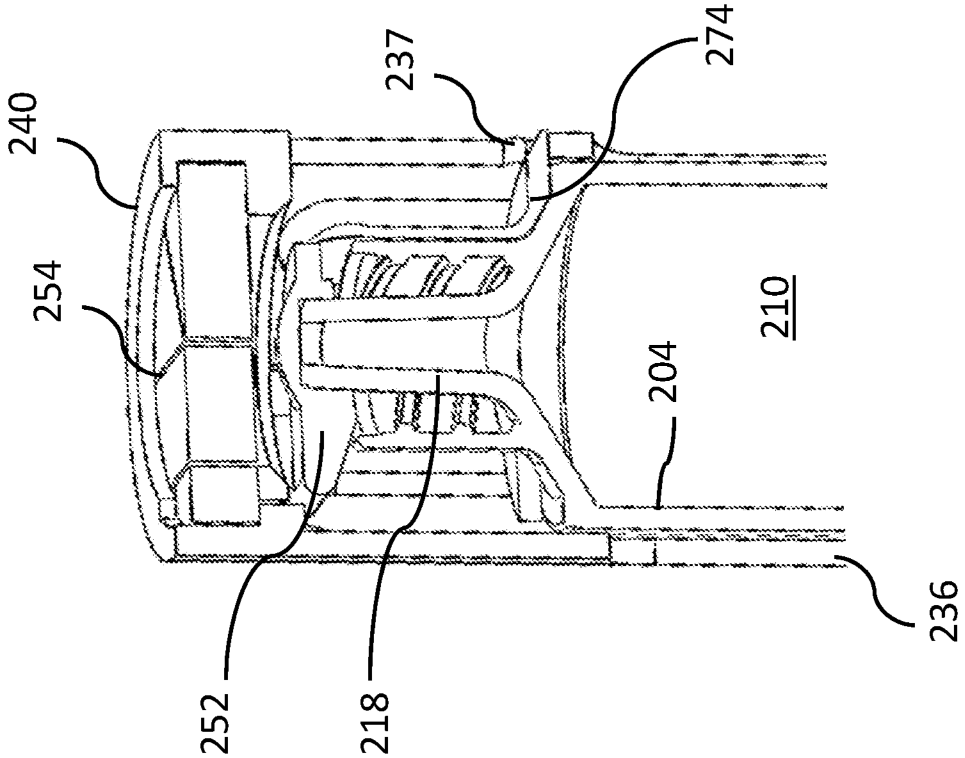
FIG. 12 is an enlarged partially cross-sectioned side elevation of the flush syringe assembly of FIG. 11 with the cap in the retracted position.
Figure 15:
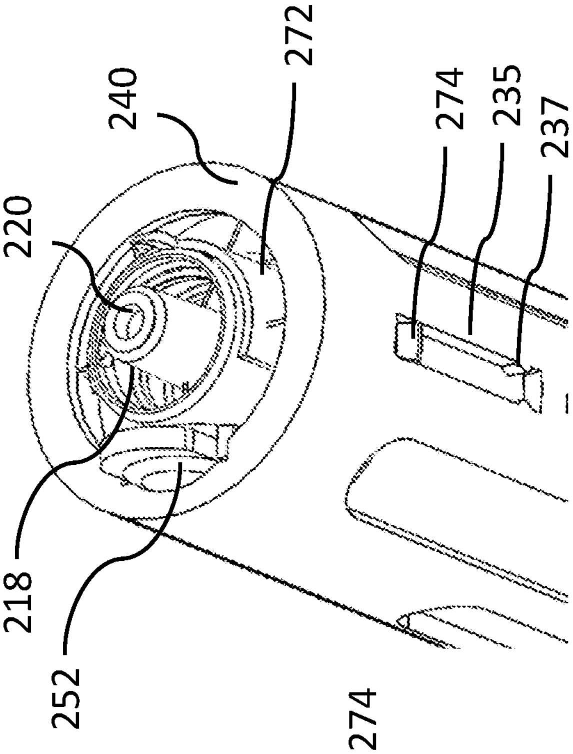
FIG. 15 is a partial perspective view of the distal end of the flush syringe assembly with the cap in the extended position
Figure 14:
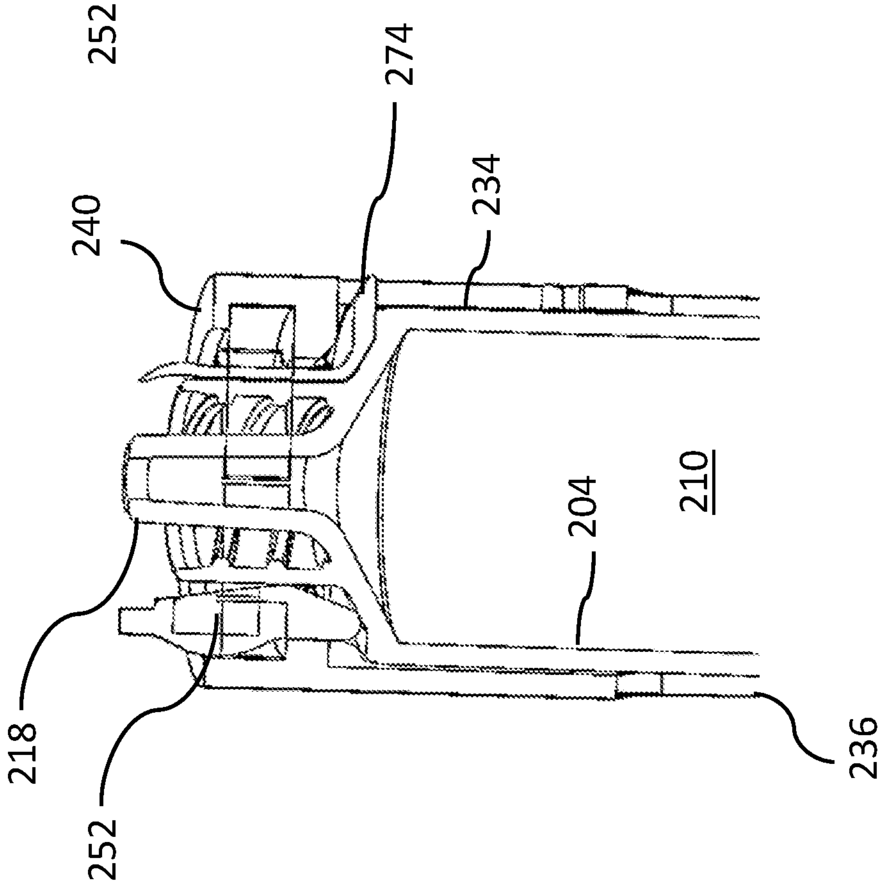
FIG. 14 is an enlarged partially cross-sectioned side elevation of the flush syringe assembly of FIG. 11 with the cap in the extended position from the distal end of the flush syringe.
Figure 16A:
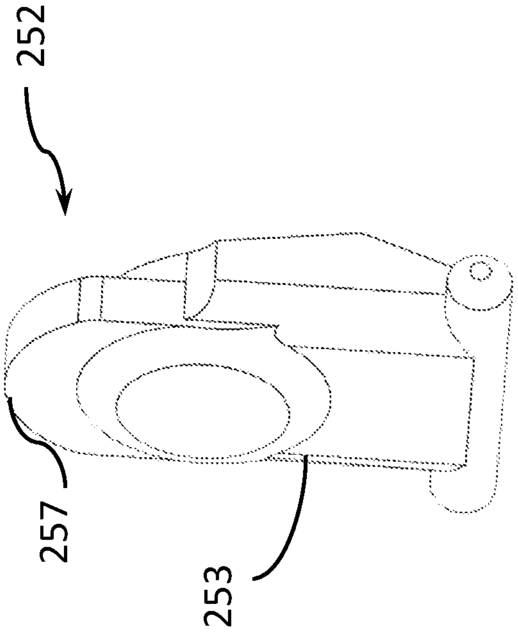
FIG. 16A is a perspective view of the distal side the cap of the flush syringe assembly of FIG. 11.
Figure 16B:
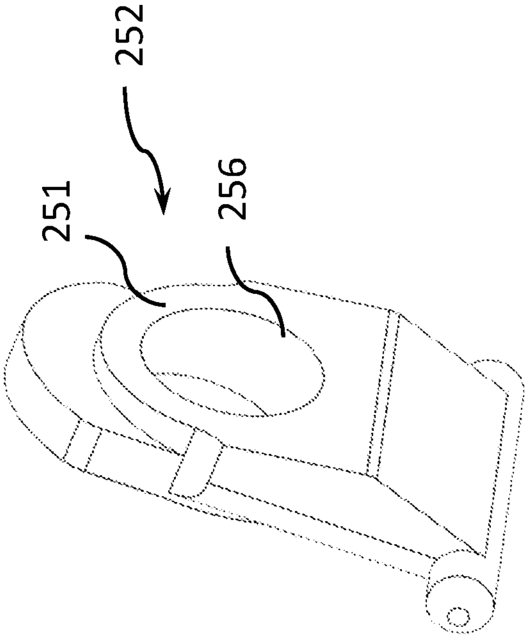
FIG. 16B is a perspective view of the proximal side of the cap of the flush syringe assembly of FIG. 11.
Figure 17:
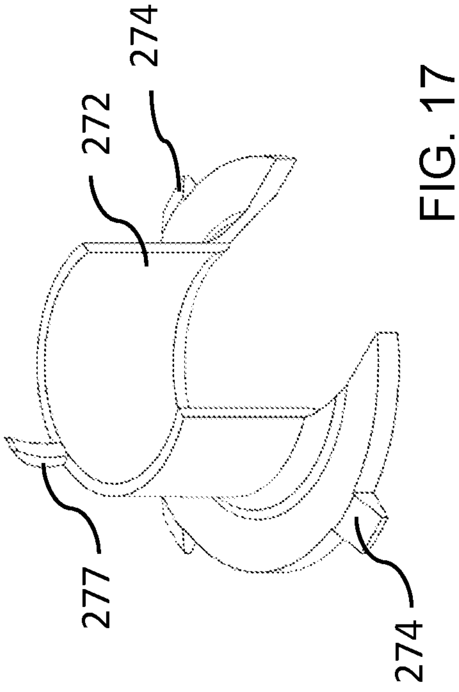
FIG. 17 is a perspective view of the alignment collar of the flush syringe assembly of FIG. 11.

Referring now to FIGS. 11 and 12, relative sliding movement of the outer sleeve 232 and the barrel 202 moves the distal tip 218 of the barrel 202 and the open distal end 238 of the outer sleeve 232 closer together, which pushes the distal tip 218, causing the distal tip to rotate the cap 252 from the first position to the second position. FIG. 13 shows the cap 252 rotated in the direction of arrow 265 from the first position 252*a* in which the cap 252 covers the distal tip 218, to position 252*b* as the cap 252 is rotated off of the distal tip to position 252*c* and then position 252*d* where the cap 252 is in the second position, which is an uncovered position and the distal tip 218 is exposed as shown in FIGS. 14 and 15. The relative sliding movement of the outer sleeve 232 and the barrel occurs when a user of the syringe assembly applies proximally directed force (in the direction of arrow 241 in FIG. 11) to the outer sleeve flange 239 while applying distally directed force (in the direction of arrow 221 in FIG. 11) to the barrel flange 219. According to one or more embodiments, a user can clean a VAD with the syringe assembly 100 and then connect the syringe assembly to the VAD using one hand. For example, a user can hold the syringe assembly with cap in the first position as shown in FIGS. 2-4 by gripping placing the outer sleeve between the index finger and middle finger of their hand. The user can then move the cap 252 and absorbent pad 254 out of the way by gripping the outer sleeve 232, applying the proximally directed force to the outer sleeve flange 239 by placing the outer sleeve between the user's fingers and pressing the barrel flange 219 into the palm of the user's hand or thumb as desired, which applies the distally directed force to the barrel flange 219. The user of the syringe assembly 200 applying the forces in this manner squeezes the outer sleeve flange 239 and barrel flange 219 towards each other, moving the cap 252 off of the distal tip 218 and exposing the distal tip 218, which can then be connected to a VAD.

In the embodiment shown in FIGS. 10-17, rotation of the cap 252 pierces the fixed seal 250*b* and pushes through the absorbent pad 254.

The syringe assembly 200 is further shown as comprising a connection collar 270 surrounding the distal tip 218 and an alignment collar 272 coaxial with the connection collar 270, the alignment collar 272 comprising a peripheral tab 274 that engages the outer sleeve 232. The outer sleeve 232 comprises a slot 235 that cooperates with the peripheral tab 274 to align the cap 252 with the open distal end 238 of the outer sleeve 232 and to guide relative sliding movement between the barrel 202 and the outer sleeve 232. In the embodiment shown and as best seen in FIG. 7, the slot 235 in the outer sleeve comprises a detent 237 to prevent unintended relative movement of the syringe barrel 202 and the outer sleeve 232. FIGS. 11 and 12 show the peripheral tab 274 below the detent 237 in the slot 235, which holds the assembly in the ready to use position. The peripheral tab 274 and the detent 237 in the slot 235 are configured so that the user must exert a sufficient amount of force to advance the peripheral tab 274 past the detent 237, causing the cap to move from the first position to the second position. FIG. 15 shows the peripheral tab 274 after the peripheral tab 274 has been advanced past the detent 237, having moved in a distal direction (indicated by arrow 221 in FIG. 11), advancing the distal tip 218 past the open distal end 238 of the outer sleeve so that the distal tip can be connected to a VAD. In one or more embodiments, the alignment collar 272 can comprise a plurality of peripheral tabs 274, for example, two, three, or more. The outer sleeve 232 can similarly comprise a plurality of slots 235 which cooperate with the peripheral tabs 274 to guide the outer sleeve 232 and the barrel 202 during relative sliding motion.

In the embodiment shown in FIGS. 10-17, the cap 252 may include a sharpened edge 257 to aid in piercing the fixed seal 250*b* as the cap 252 is moved from the first position to the second position. The alignment collar 272 may also comprise a sharpened feature 277 such as a spike, which may also pierce the fixed seal 250*b* as the user squeezes the outer sleeve flange 239 and the barrel flange 219 to activate the device to expose the distal tip 218. The absorbent pad has a thickness and may have cut pattern through the thickness to allow the cap 252 to push through the absorbent pad 254.

In use, when a user of the syringe assembly 200 peels away the removable seal 250, the absorbent pad 254 is exposed and can be used to clean or swap a VAD. During cleaning, the cap 252 is in the first position, the absorbent pad 254 is exposed through the open distal end of the outer sleeve 232. When the cleaning is completed by the user, the user can activate the device as described above to place the cap 252 is in the second position, and the cap 252 is rotated through the open distal end 238 of the outer sleeve 232 to expose the distal tip 218 of the barrel 202.

According to one or more embodiments, the removable seal of the embodiments described herein comprises an aluminum or multi-layer polymer film peel back top. The removable seal provides a liquid tight seal by a suitable adhesive that adheres the removable seal to the peripheral distal surface of the outer sleeve. The removable seal prevents the disinfectant from dissipating too quickly and facilitates long shelf life. The removable seal can be chemically-resistant, light-blocking, non-permeable, or sterile. In one or more embodiments, the connection collar comprises a Luer connector.

While not shown in the Figures, the syringe assembly according to one or more embodiments can further comprise a plunger rod comprising a distal end including a stopper slidably positioned in fluid-tight engagement with the inside surface of the barrel for drawing fluid into and driving fluid out of the chamber by movement of the stopper relative to the barrel. The plunger rod extends outwardly from the open proximal end of the barrel The absorbent pad according to one or more embodiments soaks up the disinfectant or antimicrobial agent. The disinfectant or antimicrobial agent can be a fluid or a gel selected from the group consisting of selected from the group consisting of ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorohexidine, dichlorobenzyl alcohol, dehydroacetic acid, hexetidine, triclosan, hydrogen peroxide, colloidal silver, and mixtures thereof.

The syringe assemblies described herein can be filled with flush solution using known methods. Additionally, the syringe assemblies may be provided pre-filled from the manufacturer or supplier. The flush solution may be any solution intended for flushing or maintaining performance of VAD's. The flush solution can be selected from suitable flush solutions such as saline flush solution and heparin lock flush solution. These solutions are known in the art and are readily available. An example of a saline flush solution includes, but is not limited to, 0.9% sodium chloride USP for injection. An example of a heparin lock flush solution includes but is not limited to 0.9% sodium chloride with 100 USP units of heparin sodium per mL or 10 USP units of heparin sodium per mL.

The syringe assemblies can be used in flushing a vascular access device such as a catheter or IV set. IV sets can be very complex and may include multiple injection ports, valves, and/or other components.

There are two general classifications of VAD's, peripheral catheters and central venous catheters. Peripheral catheters are used to access veins in the peripheral extremities such as the hand and arm. Peripheral catheters are relatively short in length ranging from about 14 mm to 48 mm in length, and are available in gauge sizes from about 16 to 24. It is believed that the most commonly used peripheral catheters are 20 gauge having an ID of about 0.81 mm (0.032 inch) and 22 gauge having an ID of about 0.66 mm (0.026 inch), and having a length of about 25 mm to 32 mm. As used herein, the term "peripheral catheter" is intended to refer to a 20 or 22 gauge catheter having a length of about 25 mm Central venous catheters are substantially longer than peripheral catheters and are inserted in the patient and terminate near the heart.

Another aspect of the disclosure pertains to a method of disinfecting a vascular access device. The method includes exposing an absorbent pad containing disinfectant at a distal end of a flush syringe assembly comprising a barrel having a distal tip covered by a cap, contacting the vascular access device with absorbent pad, and then rotating the cap to expose the distal tip of the barrel. The method can further comprise utilizing embodiments of the syringe assemblies described herein, for example, a syringe assembly which comprises an outer sleeve having and open distal end and a distal end face slidably engaged with the syringe barrel and the method further comprises sliding the syringe barrel and the outer sleeve with respect to each other, causing the cap to rotate away from the distal tip. Sliding the syringe barrel and the outer sleeve with respect to each other causes the cap to rotate away from the distal tip. Prior to sliding the outer sleeve and the barrel with respect to each other, a user removes a removable seal from the distal end face of the outer sleeve to expose the absorbent pad. Prior to (or after) removing the removable seal, a user can break the stopper free. After scrubbing the VAD connector, the user slides the outer sleeve to expose the syringe tip, the syringe tip is attached to the VAD connector, and the VAD is flushed. The syringe assembly is then removed after the flushing procedure and discarded.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as disclosed.

What is claimed is:

1. A flush syringe assembly comprising:

a barrel including a side wall having an outside surface, an inside surface defining a chamber for retaining fluid, an open proximal end, and a distal end including a distal wall with a distal tip extending distally therefrom having a first passageway therethrough in fluid communication with said chamber;

an outer sleeve slidably engaged with the outside surface of the barrel, the outer sleeve comprising an inner surface, an outer surface, and an open distal end comprising a peripheral distal surface;

a removable seal disposed on the peripheral distal surface; and a cap rotatably disposed between the distal tip and the open distal end of the outer sleeve and an absorbent pad containing disinfectant disposed between the removable seal and the distal tip, the cap rotatable from a first position in which the distal tip is covered by the cap and a second position in which the distal tip of the barrel is exposed through the open distal end of the outer sleeve; and a fixed seal located between the cap and the removable seal, wherein rotation of the cap causes the cap to pierce the fixed seal and move through the absorbent pad into the second position.

2. The flush syringe assembly of claim 1, wherein relative sliding movement of the outer sleeve and the barrel to move the distal tip of the barrel and the open distal end of the outer sleeve closer together causes the distal tip to rotate the cap from the first position to the second position.

3. The flush syringe assembly of claim 2, the barrel further comprising a connection collar surrounding the distal tip and an alignment collar coaxial with the connection collar, the alignment collar comprising a peripheral tab that engages the outer sleeve.

4. The flush syringe assembly of claim 3, wherein the connection collar comprises a Luer connector.

5. The flush syringe assembly of claim 3, wherein the outer sleeve comprises a slot that cooperates with the peripheral tab to align the cap with the open distal end of the outer sleeve and to guide relative sliding movement between the barrel and the outer sleeve.

6. The flush syringe assembly of claim 5, wherein the slot in the outer sleeve comprises a detent to prevent unintended relative movement of the syringe barrel and the outer sleeve.

7. The flush syringe assembly of claim 5, wherein the absorbent pad is contained within the cap.

8. The flush syringe assembly of claim 2, wherein the absorbent pad has a thickness and a cut pattern through the thickness.

9. The flush syringe assembly of claim 8, wherein rotation of the cap causes the cap to pierce the fixed seal and move through the absorbent pad into the second position.

10. The flush syringe assembly of claim 1, wherein the absorbent pad is contained within the cap.

11. The flush syringe assembly of claim 10, wherein peeling away the removable seal exposes the absorbent pad.

12. The flush syringe assembly of claim 11, wherein when the cap is in the first position, the absorbent pad is exposed through the open distal end of the outer sleeve, and when the cap is in the second position, the cap is rotated through the open distal end of the outer sleeve to expose the distal tip of the barrel.

13. The flush syringe assembly of claim 1, wherein the removable seal comprises an aluminum or multi-layer polymer film peel back top.

14. The flush syringe assembly of claim 1, wherein the outer sleeve comprises a flange at a proximal end and the barrel comprises a barrel flange at the proximal end.

15. A flush syringe assembly comprising: a barrel including a side wall having an outside surface, an inside surface defining a chamber for retaining fluid, an open proximal end, and a distal end including a distal wall with a distal tip extending distally therefrom having a first passageway therethrough in fluid communication with said chamber; an outer sleeve slidably engaged with the barrel, the outer sleeve comprising an inner surface, an outer surface, and an open distal end comprising a peripheral distal surface; a cap covering the distal tip, the cap comprising a proximal side that covers the distal dip and a distal side including an absorbent pad mounted thereon, the cap pivotally movable from a first position in which the cap covers the distal tip to a second position in which the cap is moved away from the distal tip, allowing the distal tip to be connected to a vascular access device and the cap remains connected to the outer sleeve after moving to the second position; a removable seal disposed on the peripheral distal surface; and a fixed seal located between the cap and the removable seal, wherein rotation of the cap causes the cap to pierce the fixed seal and move through the absorbent pad into the second position.

16. The flush syringe assembly of claim 15, wherein peeling away the removable seal exposes the absorbent pad.

17. The flush syringe assembly of claim 15, wherein relative sliding movement of the outer sleeve and the barrel moves the distal tip of the barrel and the open distal end of the outer sleeve closer together, which pushes the distal tip, causing the distal tip to rotate the cap from the first position to the second position.

18. A method of disinfecting a vascular access device, the method comprising:

exposing an absorbent pad containing disinfectant at a distal end of a flush syringe assembly comprising a barrel having a distal tip covered by a cap;

contacting the vascular access device with absorbent pad; and rotating the cap to expose the distal tip of the barrel, wherein the flush syringe assembly further comprises an outer sleeve having and open distal end and a distal surface slidably engaged with the syringe barrel and the method further comprises sliding the syringe barrel and the outer sleeve with respect to each other, causing the cap to rotate away from the distal tip, characterized in that the flush syringe further comprises a fixed seal located between the cap and the removable seal, wherein rotation of the cap causes the cap to pierce the fixed seal and move through the absorbent pad into the second position.

19. The method of claim 18, further comprising removing a removable seal from the distal surface of the outer sleeve to expose the absorbent pad.

* * * * *